United States Patent [19]

Taylor

[11] Patent Number: 4,522,996
[45] Date of Patent: Jun. 11, 1985

[54] β-ELIMINATING POLYMERS FOR DIFFUSION CONTROL IN PHOTOGRAPHIC PRODUCTS

[75] Inventor: Lloyd D. Taylor, Lexington, Mass.

[73] Assignee: Polaroid Corporation, Cambridge, Mass.

[21] Appl. No.: 624,826

[22] Filed: Jun. 26, 1984

Related U.S. Application Data

[62] Division of Ser. No. 454,448, Dec. 29, 1982, Pat. No. 4,458,001.

[51] Int. Cl.³ .................... C08F 228/06; C08F 226/02
[52] U.S. Cl. .................................. 526/256; 526/288; 526/301
[58] Field of Search ........................ 526/256, 288, 301

[56] References Cited

U.S. PATENT DOCUMENTS

| | | | |
|---|---|---|---|
| 3,852,073 | 12/1974 | Fitzgerald | 430/627 |
| 4,225,693 | 9/1980 | McCormick | 526/288 |
| 4,288,523 | 9/1981 | Taylor | 430/45 |
| 4,297,431 | 10/1981 | Sullivan | 430/215 |
| 4,323,644 | 4/1982 | Nokamura et al. | 430/627 |
| 4,391,895 | 7/1983 | Schwarzel et al. | 430/215 |

OTHER PUBLICATIONS

Organic Coatings and Applied Polymers Science Proceedings, vol. 46, pp. 506–513.
Preprints of Papers Presented by the Division of Organic Coatings and Plastics Chemistry at the American Chemical Society, 183rd National Meeting, Las Vegas, Nev., Mar. 25–Apr. 2, 1982.

*Primary Examiner*—Joseph L. Schofer
*Assistant Examiner*—Peter F. Kulkosky
*Attorney, Agent, or Firm*—Louis G. Xiarhos

[57] ABSTRACT

Polymerizable monomeric carbamates are disclosed. Polymers comprising recurring units from such carbamates undergo β-elimination in an alkaline environment and are useful in diffusion control layers in diffusion transfer photographic products.

10 Claims, 4 Drawing Figures

β-ELIMINATING POLYMERS FOR DIFFUSION CONTROL IN PHOTOGRAPHIC PRODUCTS

This is a division of application Ser. No. 454,448, filed Dec. 29, 1982, now U.S. Pat. No. 4,458,001.

BACKGROUND OF THE INVENTION

The present invention relates to photography and particularly to products adapted for employment in forming photographic diffusion transfer images. In particular, the present invention is directed toward novel monomers and polymers and to the use of these polymers in diffusion control layers of photographic diffusion transfer film units.

SUMMARY OF THE INVENTION

According to the present invention, there have been discovered novel monomers and polymers which comprise recurring units capable of undergoing β-elimination in an alkaline environment to convert a layer comprising one or more of said polymers from a condition of impermeability to alkali or materials soluble in or solubilized by an aqueous alkaline processing composition to a condition of substantial permeability thereto. It has also been discovered that layers comprising these novel polymers may be used as diffusion control interlayers or overcoats in photosensitive elements and negative components of diffusion transfer film units and as timing layers or overcoats in image-receiving elements and positive components of diffusion transfer film units.

It is thus an object of the present invention to provide novel monomers and polymers thereof comprising recurring units capable of undergoing β-elimination in the presence of alkali.

It is another object of the present invention to provide novel diffusion transfer photographic film units comprising at least one diffusion control layer comprising the novel polymers of the present invention.

It is another object of the present invention to provide novel diffusion control layers comprising the polymers of the present invention for use in diffusion transfer processes.

Another object of the present invention is to provide a novel image-receiving element adapted for use in diffusion transfer film units and comprising a diffusion control layer having predetermined permeability characteristics and comprising a novel polymer of the present invention.

Another object of the present invention is to provide novel integral negative-positive diffusion transfer film units comprising at least one diffusion control interlayer, timing layer, or overcoat layer comprising the novel polymers of the present invention.

Still another object of the present invention is to provide a novel photosensitive element for use in diffusion transfer processes which photosensitive element comprises a diffusion control interlayer or overcoat having predetermined permeability characteristics and comprising a novel polymer of the present invention.

Other objects of the present invention will become apparent from the description appearing hereinafter.

For a fuller understanding of the nature and objects of the invention, reference should be had to the following detailed description taken in connection with the accompanying drawings.

THE DRAWINGS

DETAILED DESCRIPTION

Figure 1:
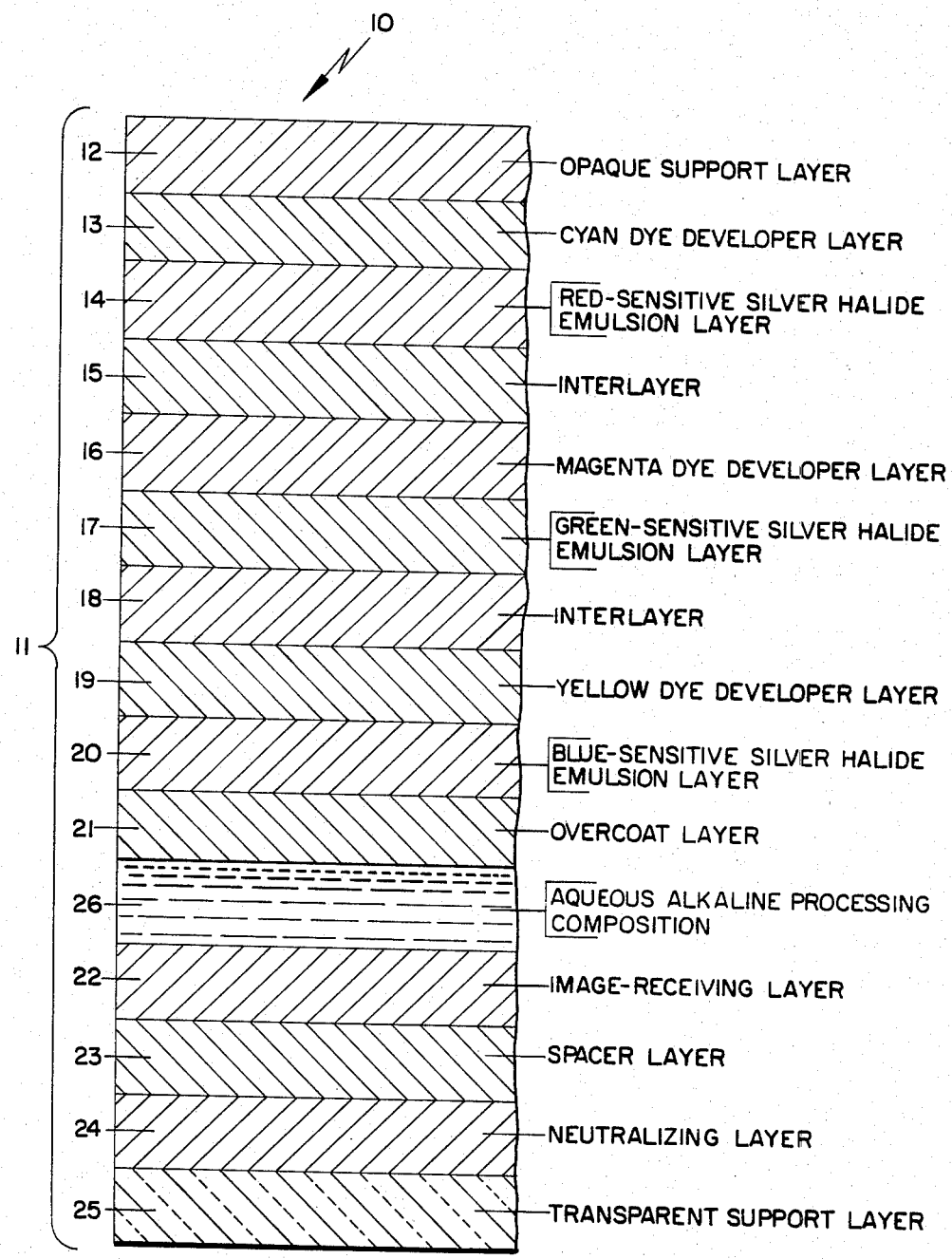
FIG. 1 is a cross-sectional view of a photographic film unit including diffusion control layers of this invention.

As mentioned hereinabove, novel polymers have been discovered which are capable of converting a layer comprising one or more of said polymers from a condition of impermeability to alkali or materials soluble in or solubilized by an aqueous alkaline processing composition to a condition of substantial permeability thereto by undergoing a β-elimination reaction in an alkaline environment. It has also been discovered that layers comprising these polymers can be used as diffusion control layers in diffusion transfer film units. These diffusion control layers have been found to be useful as overcoats or interlayers in photosensitive elements and negative components of diffusion transfer film units or as timing layers or overcoats in image-receiving elements and positive components of diffusion transfer film units. The diffusion control layers hereof function by forming an impermeable "barrier" layer which prevents passage or diffusion therethrough of either alkali or materials soluble in or solubilized by an aqueous alkaline processing composition for a predetermined length of time during processing of the film unit and then converting over a relatively short time period to a condition of substantial permeability to these materials as a result of the polymers hereof undergoing β-elimination. These diffusion control layers are thus "hold-release" layers in that materials intended to be subject to diffusion control by the layer are "held" in place for a predetermined period of time and then are "released" in substantial quantity over a relatively short time period, i.e., allowed to rapidly diffuse through the layer. This desirable "hold-release" behavior may be contrasted with the diffusion control properties of those diffusion control layers of the prior art which are not capable of undergoing a precipitous change in permeability but rather are initially permeable to some degree, and thus allow a slow leakage of material from the start of processing, and gradually become more permeable during the processing interval.

The novel polymers of the present invention comprise essential recurring units capable of undergoing β-elimination and having the formula (I)

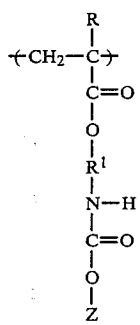 (I)

wherein R is hydrogen, halogen (e.g., chloro) or lower alkyl (e.g., methyl); $R^1$ is alkylene (e.g., ethylene); and Z is an organic moiety capable under alkaline conditions of undergoing a β-elimination reaction.

It will be seen from inspection of the recurring units of formula (I) that the polymers of the present invention are derived from monomeric compounds containing the

moiety characteristic of carbamates and that the polymers may thus be termed polycarbamates. For purposes of brevity and convenience the recurring units of formula (I) are hereinafter referred to simply as "β-elimination units".

In general, a β-elimination reaction involves the elimination or removal of two groups from a parent molecule, these groups being substituted on adjacent atoms, i.e., beta to each other. The β-elimination reaction or removal results in the formation of a more unsaturated bond, usually a double bond, between the adjacent atoms. The organic moiety Z of the polymers of formula (I) is a moiety containing the atoms requisite for the conduct under alkaline conditions of a β-elimination reaction. Typically, the organic moiety Z, hereinafter simply "a β-elimination moiety", will contain at least two interbonded carbon atoms, one of the carbon atoms containing an acid-labile proton capable of abstraction under alkaline conditions and an activating group effective to activate the β-elimination mechanism. Thus, the β-elimination moiety will contain at least the following

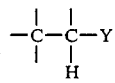

wherein is shown an abstractable acid-labile proton and wherein Y represents a β-elimination activating group which activates the β-elimination reaction with the resulting formation of a compound containing a double bond between the interbonded carbon atoms.

The β-elimination moiety Z can, for example, be the moiety

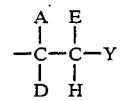

wherein is shown the abstractable proton and wherein A, D and E are independently hydrogen, methyl or phenyl, provided that not more than one of A, D and E is methyl or phenyl and Y is an activating group for the β-elimination.

Referring to a polymer comprising the recurring units of formula (I), the β-elimination reaction and mechanism involved in the case where the β-elimination moiety Z is a moiety

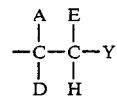

can be represented as follows:

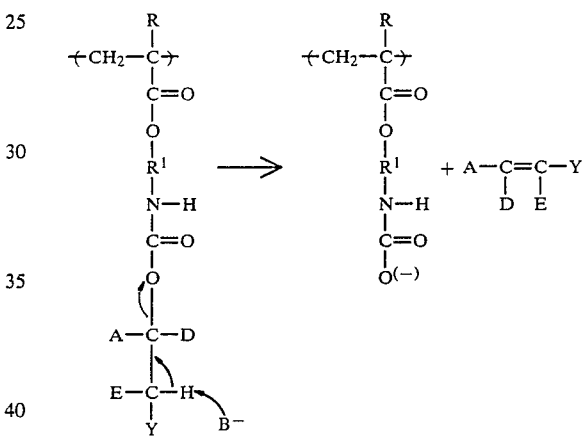

wherein $B^-$ is an anionic base. The above reaction scheme indicates that the anionic polymer unit formed by the β-elimination is effectively a leaving group removed from the parent molecule (starting polymer) in order to effect formation of the double bond of the ethylene compound

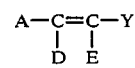

The activating group Y can be any group which is photographically innocuous and capable of stabilizing the carbanionic species formed by abstraction of the acid-labile proton by the anionic base. A study of such activating groups has been provided by J. Crosby and C. J. M. Stirling in J. Chem. Soc., B, 1970, p. 671. Activating groups which may be used in the present invention include sulfones of the formula $-SO_2W$ wherein W is aryl, aralkyl, alkaryl, alkyl, amino, or substituted amino; carbonyl groups of the formula

wherein T is hydrogen, alkyl, alkoxy, amino, or substituted amino; sulfoxide groups of the formula

wherein G is aryl, alkyl, alkaryl or aralkyl; nitro; and cyano. Preferred groups which activate the β-elimination reaction are activating groups Y of the formula —SO₂W wherein W is alkyl (e.g., methyl or ethyl).

The β-elimination moiety Z can comprise a cyclic structure. Thus, Z can be the moiety

wherein Y is a divalent radical

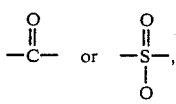

A represents the atoms necessary with Y to complete a four- to seven-membered ring structure, and D and E are independently hydrogen, methyl or phenyl, provided that no more than one of D and E is methyl or phenyl. Preferably, both D and E will be hydrogen. In the cyclic Z moiety, A can, for example, represent a divalent radical such as methylene, dimethylene, trimethylene or tetramethylene to complete, with divalent radical Y, a four-, five-, six- or seven-membered ring structure. Suitable examples of cyclic Z β-elimination moieties include

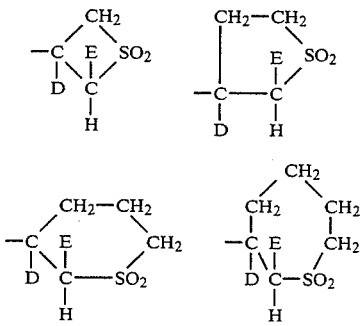

wherein D and E have the meanings aforedescribed.

The β-elimination moiety, Z, can also include cyclic structures wherein the activating group Y is a substituent. For example, such cyclic moieties are represented by the formula

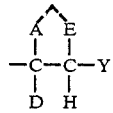

wherein A and E together represent the atoms necessary to complete with the carbon atoms to which they are bonded a five-, six- or seven-membered ring structure, D represents hydrogen, methyl or phenyl and Y is a β-eliminating activating group. Preferably, D will represent hydrogen. Y can be any of the β-elimination activating groups hereinbefore described. Examples of cyclic β-elimination moieties Z wherein the activating group Y is a ring substituent include

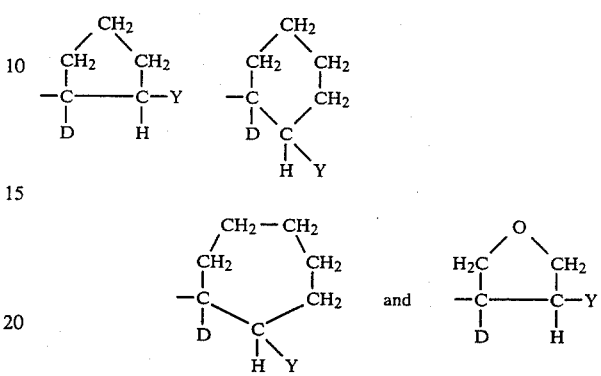

wherein D and Y have the aforedescribed meanings. Preferred Y groups are alkylsulfonyl (e.g., methylsulfonyl), alkarylsulfonyl (e.g., p-tolylsulfonyl), cyano and nitro. Preferably, D is hydrogen.

Preferred polymers of this invention include those comprising recurring units of the following formulae:

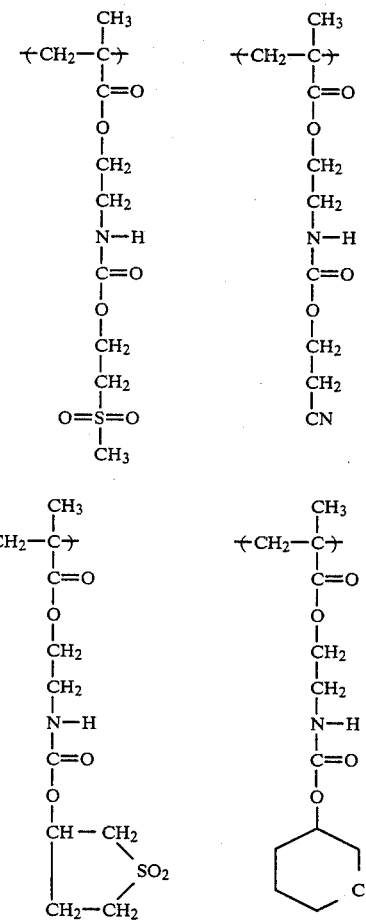

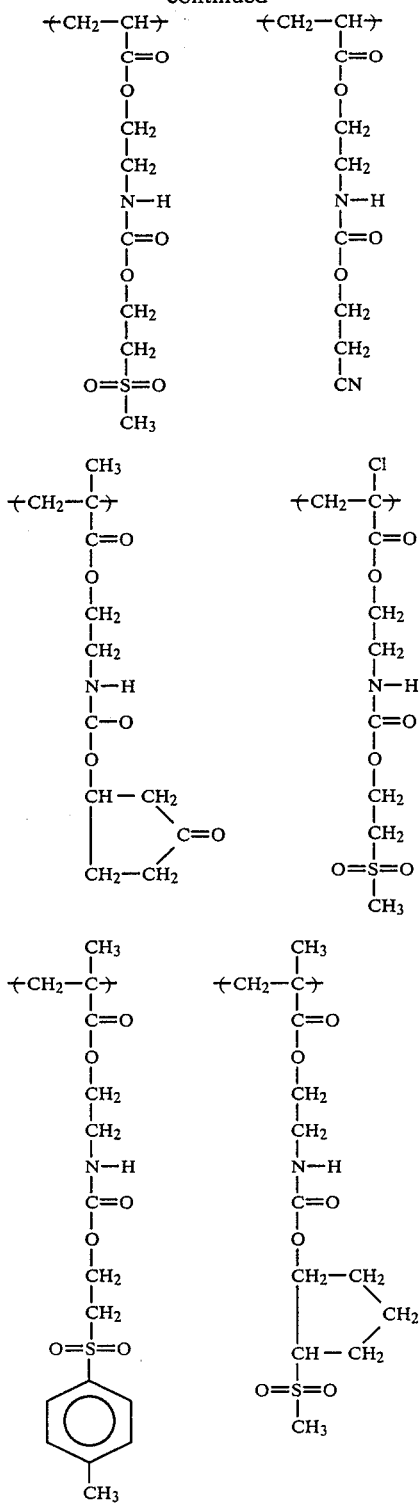

As mentioned previously, the polymers of this invention can be copolymers comprising the β-elimination monomeric units and a variety of comonomeric units incorporated into the polymer to impart thereto predetermined properties. For example, the "hold time", i.e., the time interval during which a diffusion control layer remains impermeable during processing, can be affected by the relative hydrophilicity of the layer resulting from incorporation of a given comonomer or mixture of comonomers into the β-elimination polymer. In general, the more hydrophobic the polymer, the slower will be the rate of permeation of alkali into a diffusion control layer to initiate the β-elimination reaction, i.e., the longer the hold time. Alternatively, adjustment of the hydrophobic/hydrophilic balance of the polymer by inclusion of appropriate comonomeric units may be used to impart selective permeability characteristics to a diffusion control layer as appropriate for a given usage within a film unit. For example, as detailed hereinbelow, it is highly preferred that diffusion control interlayers in the negative component of the film unit be initially substantially permeable to alkali, water, and various other components of the processing composition while substantially impermeable to the image-providing materials of the film unit up to a predetermined point in the development process. Such selective permeability may be achieved in the present invention by inclusion of appropriate comonomeric units, generally of a relatively hydrophilic nature, into the β-elimination polymers hereof or, more particularly, by "balancing" the hydrophobic and hydrophilic moieties to achieve the desired permeability.

Examples of suitable comonomers for use in the present invention include acrylic acid; methacrylic acid; 2-acrylamido-2-methylpropane sulfonic acid; N-methyl acrylamide; methacrylamide; ethyl acrylate; butyl acrylate; methyl methacrylate; N-methyl methacrylamide; N-ethyl acrylamide; N-methylolacrylamide; N,N-dimethyl acrylamide; N,N-dimethyl methacrylamide; N-(n-propyl)acrylamide; N-isopropyl acrylamide; N-(β-hydroxy ethyl) acrylamide, N-(β-dimethylamino)acrylamide; N-(t-butyl) acrylamide; N-[β-(dimethylamino)ethyl]methacrylamide; 2-[2'-(acrylamido)ethoxy]ethanol; N-(3'-methoxy propyl)acrylamide; 2-acrylamido-3-methyl butyramide; acrylamido acetamide; methacrylamido acetamide; 2-[2'-methacrylamido-3'-methyl butyramido]acetamide; and diacetone acrylamide.

As examples of useful copolymers of this invention mention may be made of:

(1) N-(methacryloxyethyl) -β-methylsulfonylethyl carbamate/styrene (70/30 parts by weight):

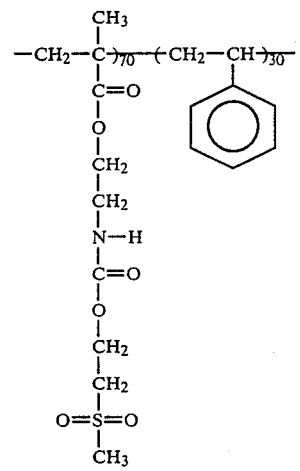

(2) N-(methacryloxethyl-β-methylsulfonylethyl carbate/methylmethacrylate (56/44 parts by weight)

(3) N-(methacryloxyethyl) -β-methylsulfonylethyl carbamate/diacetone acrylamide/styrene (56/30/14 parts by weight)

(4) N-(methacryloxyethyl)-β-methylsulfonylethyl carbamate/styrene/2-acrylamido-2-methylpropane sulfonic acid/acrylic acid (70/30/1.5/1.5 parts by weight)

(5) N-(methacryloxyethyl)-β-(p-tolyl)-sulfonylethyl carbamate/methylmethacrylate (70/30 parts by weight)

(6) N-(methacryloxyethyl)-β-cyanoethyl carbamate/methylmethacrylate (70/30 parts by weight)

The β-elimination reaction which the β-elimination polymers of the diffusion control layers of this invention undergo ensures that those materials intended to be subject to diffusion control by the diffusion control layer are "held" in place for a predetermined period of time and then "released" over a relatively short time period, the polymer layer undergoing a relatively rapid increase in hydrophilicity and water swellability and, thus, permeability as a result of the β-elimination reaction. The predetermined hold time may be adjusted as appropriate for a given photographic process by means such as controlling the mole ratio or proportion of β-elimination units in the polymer; altering the thickness of the diffusion control layer; incorporating appropriate comonomeric units into the β-elimination to impart thereto a desired hydrophobic/hydrophilic balance or degree of coalescence; utilizing different activating groups Y to affect the rate of β-elimination; or utilizing other materials, particularly polymeric materials, in the diffusion control layer to modulate the permeation therethrough of alkali or aqueous alkaline processing composition, thereby altering the time necessary for substantial β-elimination to occur. This latter means of adjusting the hold time of the layer may include, for example, utilization of a matrix polymer material having a predetermined permeability to alkali or aqueous alkaline processing composition as determined, for example, by the hydrophobic/hydrophilic balance or degree of coalescence thereof. In general, increased permeability to alkali or aqueous alkaline processing composition and, thus, a shorter hold time, may be obtained by increasing the hydrophilicity of the matrix polymer or decreasing the degree of coalescence.

In addition to affecting the hold time of the diffusion control layers of this invention, matrix polymers may also be used to modulate the permeability of the layers to alkali or materials soluble in or solubilized by an aqueous alkaline processing composition and thus affect the functionality of the layers within a film unit. For example, relatively hydrophobic matrix polymers or matrix polymers having a relatively high degree of coalescence may help to render diffusion control layers hereof substantially impermeable to alkali until β-elimination occurs, thus providing functionality to such layers as alkali neutralization timing layers or overcoat layers in image-receiving elements and positive components of diffusion transfer film units. Alternatively, relatively hydrophilic matrix polymers or matrix polymers having a relatively low degree of coalescence may help to render diffusion control layers hereof initially permeable to alkali while remaining impermeable to materials soluble in or solubilized by an aqueous alkaline processing composition, e.g., image dye-providing materials, until β-elimination occurs, thus providing functionality to such layers as interlayers or overcoat layers in photosensitive elements and negative components of diffusion transfer film units.

Utilization of matrix polymers can thus provide an alternative or complementary means to the above-mentioned use of suitable comonomers in the β-elimination copolymers hereof as a method of modulating the hold time or functionality of the diffusion control layers of this invention. It will be understood, however, that the β-elimination reaction is necessary to achieve the relatively rapid change in permeability of the layer.

Matrix/β-elimination polymer systems adapted to utilization in a diffusion control layer may be prepared by physical mixing of the respective polymers, or by preparation of the matrix polymer in the presence of the β-elimination polymer. As disclosed in U.S. Pat. No. 4,297,431 of Charles Sullivan, issued Oct. 27, 1981, a preferred matrix/β-elimination polymer system comprises the system whereby a β-elimination polymer is formed in the presence of a preformed matrix polymer. Polymers which may be used as matrix polymers will generally be copolymers which comprise comonomeric units such as acrylic acid; methacrylic acid; methylmethacrylate; 2-acrylamido-2-methylpropane sulfonic acid; acrylamide; methacrylamide; N,N-dimethylacrylamide; ethylacrylate; butylacrylate; diacetone acrylamide; acrylamido acetamide; and methacrylamido acetamide. The comonomeric units, as well as the ratios thereof, should be chosen on the basis of the physical characteristics desired in the matrix polymer and in the diffusion control layer in which it is to be utilized. For example, a more hydrophilic and thus a generally more permeable matrix material can be had by increasing the respective ratio of hydrophilic comonomers, such as acrylic acid or methacrylic acid, within the matrix polymer.

Matrix polymer/β-elimination polymer systems useful in the present invention include those listed below wherein MEMSEC designates N-(methacryloxyethyl)-β-methylsulfonylethyl carbamate, MEAPC designates N-methacryloxyethyl-2-acetylpropyl carbamate, MESC designates N-(methacryloxyethyl)-3-sulfonlanyl carbamate, STY designates styrene, DAA designates diacetone acrylamide, BA designates butyl acrylate, AA designates acrylic acid, MMA designates methyl methacrylate and AMPS designates 2-acrylamido-2-methylpropane sulfonic acid. In the matrix systems listed below the specified β-elimination polymer was polymerized in the presence of the specified preformed matrix polymer. All ratios and proportions are in parts by weight:

| Matrix System | Components |
| --- | --- |
| A | 70 parts of a 48.9/42.6/8/0.5 matrix copolymer of DAA/BA/AA/AMPS and 30 parts of 70/30 poly(MEAPC-co-DAA) |
| B | 70 parts of a 48.9/42.6/8/0.5 matrix copolymer of DAA/BA/AA/AMPS and 20 parts of 80/20 poly(MEMSEC-co-STY) |
| C | 70 parts of a 48.9/42.6/8/0.5 matrix copolymer of DAA/BA/AA/AMPS and 20 parts of 56/14/30 poly(MEMSEC-co-STY-co-DAA) |
| D | a mixture of 65 parts of 50.5/44/5/0.5 copolymer of DAA/BA/AA/AMPS; and 35 parts of a matrix system consisting of 78 parts of 48.9/42.6/8/0.5 matrix copolymer of DAA/BA/AA/AMPS and 22 parts of 80/20 poly(MEMSEC-co-STY). |
| E | 70 parts of a 48.9/42.6/8/0.5 matrix copolymer of DAA/BA/AA/AMPS and 30 parts |

| Matrix System | Components |
|---|---|
| | -continued |
| | of 80/20 poly(MESC-co-MMA) |

The novel polymers hereof can be utilized in a number of diffusion transfer products and processes based upon imagewise transfer of a diffusible image-providing material, e.g., a diffusible dye, dye intermediate, or soluble silver complex. The diffusion transfer film units of the present invention comprise as essential layers, a support layer; at least one photosensitive silver halide emulsion layer having associated therewith a diffusion transfer process image-providing material; an alkaline processing composition permeable image-receiving layer; and at least one diffusion control layer comprising the novel polymers of this invention. Following photoexposure, the silver halide emulsion is developed with an aqueous alkaline processing composition and, as a function of development, an imagewise distribution of diffusible image-providing material is formed which is transferred, at least in part, to the superposed image-receiving layer. The diffusion control layers of such film units may be used to control diffusion of alkali or of the image-providing material in accordance with the disclosures contained herein.

Film units within the present invention include those wherein the silver halide emulsion layers and the image-receiving layer are initially contained in separate elements. Such film units may thus comprise (a) a photosensitive element comprising a support layer which is preferably opaque and a negative component comprising at least one photosensitive silver halide emulsion layer having associated therewith a diffusion transfer process image-providing material; (b) an image-receiving element comprising a support layer which may be opaque or transparent as appropriate for a given process and a positive component comprising an image-receiving layer; and (c) a diffusion control layer comprising the polymers of this invention in at least one of said photosensitive element or image-receiving element. The respective elements may be brought into superposition subsequent or prior to exposure. Subsequent to exposure, an aqueous alkaline processing composition is distributed between the superposed elements to initiate development. If the image-receiving element provides an opaque reflective background, the image formed may be viewed as a reflection print upon separation of the elements. By using a transparent image-receiving element, the resultant image may be viewed as a transparency upon separation of the elements. Alternatively, if the photosensitive element and/or processing composition contains a light reflecting layer, e.g., a white pigment such as titanium dioxide, the image may be viewed as a reflection print against the background provided by the light-reflecting layer, without separation of the elements. The photosensitive element may also comprise a neutralization layer, e.g., an acid polymer layer, and a timing layer positioned between the support layer and the negative component with the neutralization layer positioned adjacent the support. By conduct of a neutralization reaction between the acid-reactive sites of the neutralization layer and the alkali provided by the processing composition the environmental pH of the film unit may be lowered, thus providing benefits detailed hereinbelow. The timing layer functions to prevent premature pH reduction by slowing diffusion of the alkali toward the neutralization layer.

The diffusion control layers of this invention can also be used in diffusion transfer film units wherein the photosensitive layers and image-receiving layer are in a single element, i.e. integral negative-positive film units wherein the negative and positive components are contained in a photosensitive laminate or otherwise retained together in a superposed relationship at least prior to exposure. For example, the diffusion control layers herein can be used in integral film units of the type described in detail in U.S. Pat. No. 3,415,644, which film units are particularly adapted for formation of color images. Film units of this type include, for example, those comprising: (a) a photosensitive laminate comprising a composite structure containing, in sequence, an opaque support layer, preferably an actinic radiation-opaque flexible sheet material, a negative component comprising at least one photosensitive silver halide emulsion layer having associated therewith an image dye-providing material, a positive component comprising an image-receiving layer dyeable by the image dye-providing material, and a transparent support layer, preferably an actinic radiation transmissive flexible sheet material, the photosensitive laminate also comprising a diffusion control layer comprising the polymers of the present invention; (b) means retaining an aqueous alkaline processing composition integrated with the film unit so that the processing composition can be distributed between the negative and positive components. In this type of film unit a light-reflecting pigment is preferably provided by the processing composition such that the distribution of the processing composition between the negative and positive components provides a light-reflecting layer against a dye image formed in the image-receiving layer can be viewed without separation of the components.

The diffusion control layers of this invention can also be used in integral negative-positive film units of the type described in U.S. Pat. No. 3,594,165. Film units of this type include, for example, those comprising: (a) a photosensitive laminate comprising, in sequence, a transparent support layer, preferably an actinic radiation transmissive flexible sheet material, a positive component comprising an image-receiving layer, a processing composition permeable, light-reflecting layer against which a dye image formed in the image-receiving layer can be viewed, and a negative component comprising at least one photosensitive silver halide emulsion layer having associated therewith an image dye-providing material; (b) a transparent sheet superposed substantially coextensive the surface of the photosensitive laminate opposite the transparent layer; (c) means retaining an aqueous alkaline processing composition, which includes an opacifying agent, integrated with the film unit such that the processing composition can be distributed between the photosensitive laminate and the transparent sheet; and (d) a diffusion control layer comprising a polymer of the present invention, which layer may be a component of the photosensitive laminate or a coating on that side of the transparent sheet contiguous the photosensitive laminate. Color images formed within the image-receiving layer can be viewed against the background of the light-reflecting layer without separation of the transparent sheet from the photosensitive laminate.

Multicolor images may be prepared in the film units of the present invention which comprise at least two selectively sensitized silver halide emulsion layers, each associated with an image dye-providing material which provides an image dye possessing spectral absorption characteristics substantially complementary to the predominant sensitivity range of its associated emulsion. The most commonly employed negative components for forming multicolor images are of the tripack structure and contain blue, green, and red sensitive silver halide layers each having associated therewith in the same or a contiguous layer a yellow, a magenta, and a cyan image dye-providing material respectively. It is preferred that each of the silver halide emulsion layers, and its associated image dye-providing material, be spaced from the remaining emulsion layers, and their associated image dye-providing materials, by separate alkaline solution permeable interlayers, such as those provided by the instant invention.

As disclosed in U.S. Pat. No. 2,983,606 and a number of other patents, image dye-providing materials which are particularly useful in forming color images by diffusion transfer are the dye developers, i.e., compounds which contain, in the same molecule, both the chromophoric system of a dye and also a silver halide developing function. In a typical diffusion transfer system, each dye developer is associated with a separate silver halide emulsion layer and is, most preferably, substantially soluble in the reduced form only at the first pH provided by the processing composition, possessing subsequent to photoexposure or processing a spectral absorption range substantially complementary to the predominant sensitivity range of its associated emulsion. Following photoexposure, the processing composition is applied and permeates the emulsion layers to initiate development of the latent image contained therein. The dye developer is immobilized or precipitated in exposed areas as a consequence of the development of the latent image. In unexposed and partially exposed areas of the emulsion, the dye developer is unreacted and diffusible and thus provides an imagewise distribution of unoxidized dye developer dissolved in the liquid processing composition, as a function of the point-to-point degree of exposure of the silver halide emulsion. At least part of this imagewise distribution of unoxidized dye developer is transferred, by imbibition, to a superposed image-receiving layer, said transfer substantially excluding oxidized dye developer. The image-receiving layer receives a depthwise diffusion, from the developed emulsion, of unoxidized dye developer without appreciably disturbing the imagewise distribution thereof to provide the reversed or positive color image of the developed image. The image-receiving layer may contain agents adapted to mordant or otherwise fix the diffused, unoxidized dye developer. Subsequent to substantial transfer image formation, it is preferred that the environmental pH of the film unit be adjusted downward to a second pH at which the residual dye developers remaining within the negative structure are precipitated or otherwise rendered non-diffusible in either their reduced or oxidized state. The pH adjustment is generally accomplished by means of an acid neutralization layer, preferably a polymeric acid layer, as detailed hereinbelow.

For purposes of illustration, the present invention will hereinafter be described in terms of dye developers which function as described above, although no limitation of the invention to the illustrative image dye-providing materials is intended.

As illustrated in the accompanying drawings, FIG. 1 sets forth a perspective view of an integral film unit of the type described in referenced U.S. Pat. No. 3,415,644, shown with the processing composition 26 distributed between the negative and positive components. Film unit 10 comprises photosensitive laminate 11 including in order, opaque support layer 12; cyan dye developer layer 13; red-sensitive silver halide emulsion layer 14; interlayer 15; magenta dye developer layer 16; green-sensitive silver halide emulsion layer 17; interlayer 18; yellow dye developer layer 19; blue-sensitive silver halide emulsion layer 20; overcoat layer 21; image-receiving layer 22; spacer layer 23; neutralizing layer 24; and transparent support layer 25. Following photoexposure through transparent support layer 25, processing composition 26, initially retained in a rupturable container (not shown) is distributed between overcoat layer 21 and image-receiving layer 22 to initiate development of the silver halide emulsion layers. It is preferred that processing composition 26 contains an opacifying agent of the type described for example, in U.S. Pat. No. 3,647,437, such that the layer of processing composition 26 is able to prevent further exposure of the photosensitive layers of the film unit during the processing of the film unit outside of the camera. As a consequence of development, an imagewise distribution of diffusible dye developer is formed which is transferred, at least, in part to image-receiving layer 22. The layer provided by processing composition 26 preferably comprises a light-reflecting pigment, such as titanium dioxide, against which the color image formed in image-receiving layer 22 can be viewed. Subsequent to substantial transfer image formation, a sufficient portion of the alkali provided by processing composition 26 permeates image-receiving layer 22 and spacer layer 23, to gain access to neutralizing layer 24 whereupon neutralization of the alkali occurs to lower the pH of the system to a level at which the dye developers are insoluble and non-diffusible, to provide thereby a stable color transfer image.

Rather than being positioned between image-receiving layer 22 and support layer 25, spacer layer 23 and neutralizing layer 24 may be disposed intermediate support layer 12 and cyan dye developer layer 13, with neutralizing layer 24 positioned adjacent to support layer 12. In this embodiment, the alkali provided by processing composition 26 permeates layers 13 through 21 and spacer layer 23 to gain access to neutralizing layer 24 whereupon neutralization of the alkali is effected as described hereinabove.

With multicolor diffusion transfer products such as those described above, undesirable inter-image effects may occur whereby a given dye developer or other image dye-providing material is controlled as a result of association with a silver halide emulsion layer other than the one with which it was initially associated in the film unit. This unintended associative relationship generally results from migration of the image dye-providing material to a silver halide layer other than the one with which it is initially associated prior to development of this "wrong" emulsion layer. As a result of this premature migration, the image dye-providing material may acquire diffusion characteristics opposite to those it would normally possess had it remained in association with its intended controlling silver halide layer. For example, if a dye developer prematurely migrates to a silver halide layer other than the one with which it is initially associated, it may undergo oxidation to a non-diffusible species as a function of the development of this "wrong" layer and will be rendered incapable of transferring as intended to the image-receiving layer. As a result, accuracy in color reproduction and color saturation within the transfer image will be adversely affected. In addition, a portion of a second dye developer which should have undergone oxidation as a function of the development of this "wrong layer" remains in a reduced and diffusible state and, thus, may transfer to contaminate the resultant color transfer image. These inter-image effects may be more specifically exemplified by reference to FIG. 1. If it is possible for the magenta dye-developer of layer 16 to back-diffuse to red sensitive silver halide emulsion layer 14 before substantial development of this layer and resultant substantial formation of an imagewise distribution of the cyan dye developer in layer 13, some of the magenta dye developer may become oxidized and rendered non-diffusible as a function of red exposure and development of the red sensitive emulsion layer. Thus, there is produced a loss in magenta dye density in the transfer image. Moreover, that portion of cyan dye developer which should have been oxidized in preference to the magenta dye developer remains in the reduced form and may diffuse to image-receiving layer 22 with resultant cyan dye contamination of the transfer image. Thus, accurate color reproduction of a photographed object is hindered by such inter-image effects.

To obviate or minimize inter-image effects, diffusion control layers hereof may be employed as interlayers positioned between the respective silver halide layers, and their associated dye developers, such as interlayers 15 and 18 in FIG. 1. The $\beta$-elimination step undergone by the $\beta$-elimination polymer(s) within these layers ensures a delay in permeability of these layers during initial processing of the film unit and thus "holds" the dye developer and substantially prevents diffusion to unassociated silver halide layers at least until after substantial development of these layers and formation of the intended imagewise distributions of the dye developers. The "release" of the diffusible dye developers should occur prior to substantial fogging of the emulsion layer with the most rapid fogging rate. It will be appreciated that the "hold-release" behavior of the interlayers of this invention provides advantages over those interlayers which allow a slow leaking of dye developer at the start of the processing interval in that the dye developers are better confined to their associated emulsion layer during the critical initial development interval and then released rapidly and in substantial quantity so as to allow rapid and essentially simultaneous transfer of the color image-forming materials.

In addition to minimizing the above described inter-image effects, interlayers comprising the polymers of this invention may be used to provide increased capacity for accurate color reproduction over a range of temperatures in general, the lowering of the temperature at which processing occurs slows both the rate of development and the rate of dye diffusion. If the respective rates are slowed disproportionately, i.e., if the decrease in the development rate is proportionately greater than the decrease in the rate of diffusion, color reproduction may be adversely affected by diffusion of the dye away from its associated emulsion layer prior to substantial development of that layer. This type of premature migration may be minimized by use of interlayers comprising the polymers of this invention which have been found to provide markedly longer "hold" times at lower temperatures, e.g., 7° C. relative to the "hold" time observed at higher temperatures, e.g., 24° C. Thus, the interlayers may be utilized to hold the dye developer in association with the silver halide emulsion for longer time periods at lower temperatures to accommodate the system to slower development rates at these temperatures while allowing for a proportionately faster "release" as the temperature and development rate increase.

The polymers of this invention useful as interlayer materials as described hereinabove can also be utilized in overcoat layers of photosensitive elements or negative component overcoat layers such as overcoat layer 21 in FIG. 1. Such overcoat layers can be used, for example, to prevent premature migration of the dye developer most proximate to the distributed processing composition or to provide a means by which the various color image-forming materials may be made available essentially simultaneously to the mordant sites within the image-receiving layer.

The processing compositions employed in diffusion transfer processes of the type contemplated herein usually are highly alkaline, having a pH in excess of 12 and frequently in excess of 14 or higher. In general, the highly alkaline environment facilitates the conduct of dye diffusion to provide satisfactory diffusion rates and image dye densities. As disclosed in U.S. Pat. No. 3,362,819 it is highly desirable that the environmental pH of the film unit be lowered to at least 11 or lower subsequent to substantial transfer image formation to achieve improved stability of the dye image. U.S. Pat. No. 3,415,644 discloses that in integral film units wherein the negative and positive components remain in a superposed contiguous relationship subsequent to substantial transfer image formation, an in-process adjustment of the environmental pH of the film unit from a pH at which transfer processing is operative to a pH at which dye transfer is inoperative subsequent to substantial transfer image formation is highly desirable in order to achieve a more stable dye transfer image in terms of the chemical and light stability of the image dye molecules and in terms of preventing post-processing transfer of residual image dye-providing materials within the negative structure to the image-receiving layer.

As disclosed in previously referenced U.S. Pat. No. 3,362,819, reduction in the environmental pH of the film unit is preferably achieved by conduct of a neutralization reaction between the alkali provided by the processing composition and a layer comprising immobilized acid reactive sites, i.e., a neutralization layer. Preferred neutralization layers are those comprising a polymeric acid such as cellulose acetate hydrogen phthalate; polyvinyl hydrogen phthalate; polyacrylic acid; polystyrene sulfonic acid; and partial esters of polyethylene/maleic anhydride copolymers.

Premature pH reduction, as evidenced, for example, by a decrease in image dye density, can be prevented by disposing intermediate the neutralization layer and the distributed processing composition a spacer or timing layer which slows diffusion of the alkali toward the neutralization layer. As indicated hereinabove, diffusion control layers of this invention may be used as such timing layers, forming an alkali impermeable barrier for a predetermined time interval and then converting to a relatively alkali permeable condition upon occurrence of $\beta$-elimination to allow the alkali access to the neutralization layer in a rapid and quantavitely substantial fashion.

The timing layers comprising the β-elimination polymers hereof can be used in image-receiving elements of the type disclosed in U.S. Pat. No. 3,362,819 or as a component part of the positive component of integral negative-positive film units of the type disclosed in previously referenced U.S. Pat. Nos. 3,415,644 and 3,594,165. Alternatively, the timing and neutralization layers may be associated with the negative component as is disclosed, for example, in U.S. Pat. Nos. 3,362,821 and 3,573,043. In film units of the type disclosed in referenced U.S. Pat. No. 3,594,165, these layers may also be carried by the transparent sheet employed to facilitate application of the processing composition.

Figure 2:
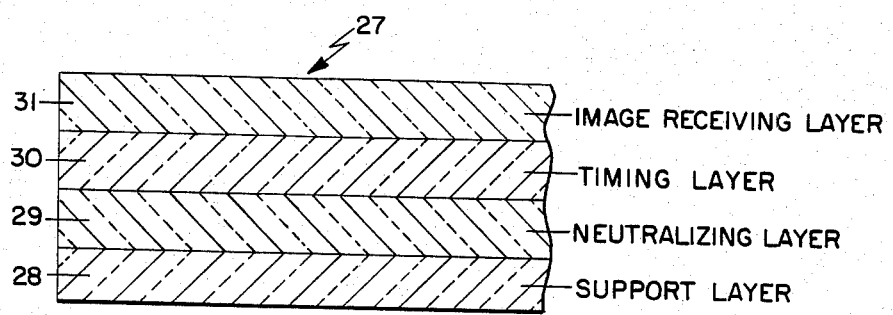
FIG. 2 is a cross-sectional view of an image-receiving element including a diffusion control timing layer of this invention.

Illustrated in FIG. 2 is an image-receiving element of the present invention. Image-receiving element 27 comprises in order a support layer 28, a neutralizing layer 29, a spacer or timing layer 30 comprising a β-elimination polymer of the present invention, and an image-receiving layer 31. During processing the image-receiving layer is situated contiguous the layer of processing composition. The processing composition penetrates image-receiving layer 31 to provide a sufficient pH for image formation therein and is then subsequently neutralized by penetrating through timing layer 30 upon β-elimination of the diffusion control polymer contained therein to gain access to neutralizing layer 29.

As indicated previously, the permeability of the diffusion control layers of this invention to alkali may be controlled in a predetermined manner by the use of comonomeric units which provide to the polymer a suitable hydrophilic/hydrophobic balance and/or a suitable degree of coalescence or by the use of a matrix material providing the required hydrophilicity or coalescence. In general, increased hydrophobicity and coalescence will render the diffusion control layer relatively less permeable to alkali and to the processing composition prior to the β-elimination reaction.

In a further embodiment of the present invention, an overcoat layer comprising the polymers hereof may be provided to the image-receiving element or positive component of the film unit contiguous the image-receiving layer and opposite the neutralization layer. Overcoat layers of this type in this position within the film unit may function to control diffusion of alkali or materials soluble in or solubilized by an aqueous alkaline processing composition.

The permeation characteristics of the polymers hereof utilized in timing layers can be evaluated by measuring the time necessary for downward adjustment of the environmental pH to a predetermined lower level as evidenced by color transition of an indicator dye, preferably initially contained in the processing composition, from a colored form at the initially high processing composition pH to a colorless form at said predetermined lower pH level. Evaluations of this type may be carried out utilizing a test structure comprising in order a support, a polymeric acid layer, a test timing layer, and an image-receiving layer. A transparent cover sheet is superposed coextensive the test structure contiguous to the image-receiving layer and an alkaline processing composition comprising an indicator dye which is highly colored at a pH of 12 or higher and colorless below a predetermined lower pH level of about 9 or 10 is spread between the cover sheet and the image-receiving layer. The indicator dye remains colored, and may be viewed as such through the transparent cover sheet, until the alkali penetrates through the test timing layer to gain access to the polymeric acid whereupon neutralization of a substantial portion of the alkali present occurs to lower the pH to a level at which the indicator dye is colorless. The measurement of the time necessary for substantial "clearing" of the indicator is generally referred to as the "clearing time". Test structures comprising timing layers which allow a slow initial leakage of alkali and gradually become more permeable show no precipitous change in color but rather a gradual clearing while structures comprising the timing layers described herein will show a precipitous change in color after an initial delay evidencing the rapid change in alkali permeability undergone by the timing layer upon β-elimination.

Figure 3:
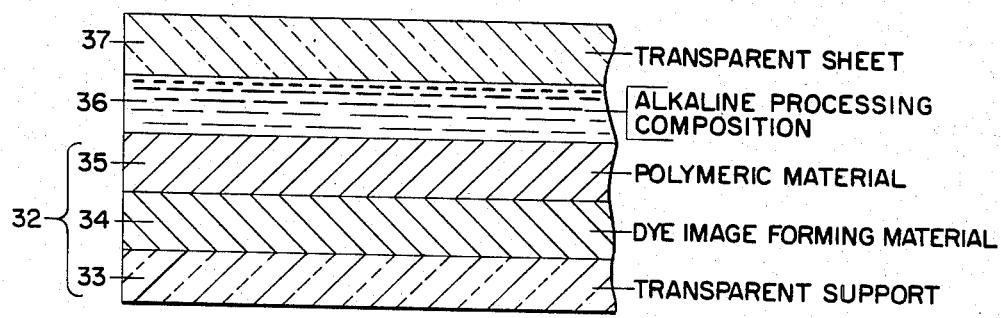
FIG. 3 illustrates a model arrangement for measuring the "hold-time" of interlayers of this invention.

The capacity of diffusion control layers comprising polymers hereof to delay permeation therethrough of dye image-providing materials until conversion by β-elimination to a relatively dye-permeable condition can be evaluated by utilization of the test structure shown in FIG. 3. In accordance with such structure, transfer of the image dye-providing material through the test diffusion control layer is monitored in relation to time. The "hold-release" properties of the β-elimination polymer test material can be evaluated in simulation of the functioning of the material, e.g., an interlayer in a photosensitive element. Such test structure and a suitable method of evaluation are set forth in detail in Example 6.

The polymers of the present invention can be prepared by polymerization in known manner of a polymerizable monomeric carbamate of the formula (III).

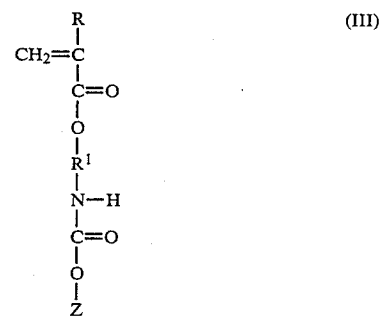

(III)

wherein R, R¹ and Z have the meanings aforedescribed. The monomeric carbamate of formula (III) can be suitably prepared by reaction of a polymerizable isocyanato ester of acrylic, methacrylic or 2-chloroacrylic acid having the formula (IV):

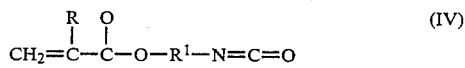

(IV)

(wherein R and R¹ are as previously defined) with an alcohol of the formula Z-OH wherein Z has the aforedescribed meaning. For example, the alcohol can have the formula (V)

(V)

(wherein each of A, D, E and Y have the meanings aforedescribed). This reaction is illustrated by reference to the following reaction scheme which shows the reaction of β-cyanatoethyl methacrylate and hydroxyethylmethylsulfone to form N-(methacryloxyethyl)-β-methylsulfonylethyl carbamate:

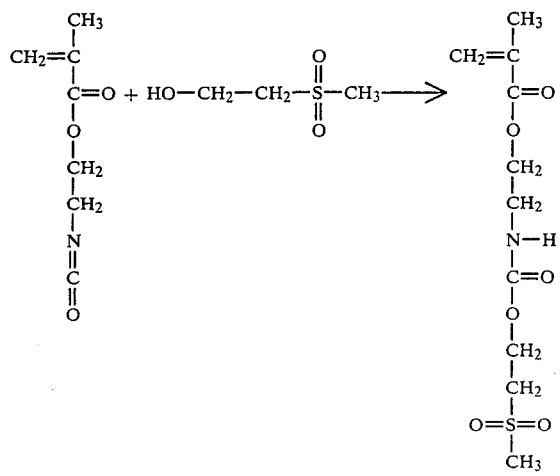

The polymerizable isocyanato esters (IV) utilized as starting materials for the production of the polymerizable monomeric carbamate compounds (III) of the invention include the isocyanatoalkyl esters of such ethylenically unsaturated acids as acrylic acid, methacrylic acid and 2-chloroacrylic acid.

Suitable isocyanoalkyl esters are the β-isocyanatoethyl esters such as the β-isocyanatoethyl esters of these ethylenically unsaturated acids. A preferred starting material is β-isocyanatoethyl methacrylate which can be effectively utilized for the production of monomeric carbamate compounds of the invention. The isocyanatoalkyl ester starting materials (IV) are known compounds and their method of preparation is described, for example, in U.S. Pat. No. 2,718,516 (issued Sept. 20, 1955 to N. M. Bortnick).

Alcohol compounds useful for the production of the monomeric carbamate compounds of formula (III) include any of those having the aforesaid formula Z-OH. Examples of aliphatic alcohols of the formula

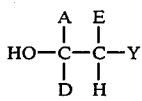

wherein A, D and E represent hydrogen, methyl or phenyl, except that not more than one of A, D and E is methyl or phenyl, include such substituted ethanol compounds as hydroxyethylmethylsulfone, p-tolylsulfonylethanol and β-hydroxypropionitrile. Cyclic alcohols wherein the activating group is a part of or is attached to a cyclic ring include such alcohols as 3-hydroxythietane dioxide; 3-hydroxy-sulfolane, 3-hydroxy-thiane dioxide; 3-hydroxy-cyclopentanone; 3-hydroxy-cyclohexanone; 1-cyano-2-hydroxy-cyclopentane; 1-hydroxy-2-methylsulfonyl cyclopentane; 1-hydroxy-2-(p-tolylsulfonyl)cyclohexane; and 3-hydroxy-4-(methylsulfonyl)-tetrahydrofuran.

The monomeric carbamate compounds of formula (III) can be prepared in any of a variety of inert solvents. It will be appreciated that isocyanate groups exhibit reactivity toward compounds having a labile proton and, accordingly, hydroxyl-containing or amine-containing solvent materials will be desirably avoided. Suitable solvents include tetrahydrofuran, chloroform, dichloromethane, dimethylformamide, benzene, dioxane, toluene, acetone, methylethylketone, and ethyl acetate. The reaction may be conducted over a temperature range of about 0° C. to about 100° C. and preferably about 15° C. to about 40° C. In general, the reaction can be facilitated by use of a tin catalyst such as stannous octanoate, a tertiary amine catalyst such as triethylamine, a 4-dialkylaminopyridine catalyst, e.g., 4-(N,N-dimethylamino)pyridine or 4-pyrrolidinopyridine. It has been found that the reaction proceeds with facility at ambient temperatures of about 25° C. to 50° C. in the presence of the above-mentioned 4-dialkylaminopyridine catalyst. If desired, a small amount of polymerization inhibitor such as hydroquinone or t-butylpyrocatechol can also be present during the reaction.

The monomers prepared by any of the above methods may be polymerized according to different polymerization techniques such as bulk, solution, suspension, or emulsion polymerization. In addition, the polymerization may be conducted in the presence of other suitable polymers, i.e., a polymeric matrix material, to prepare a matrix system which may be used as a diffusion control layer. The polymerization can be initiated chemically, e.g., by suitable free radical or redox initiators or by other means such as heat or incident radiation. As examples of chemical initiators, mention may be made of azobisisobutyronitrile, potassium persulfate, sodium bisulfite, benzoyl peroxide, diacetyl peroxide, hydrogen peroxide, and diazoaminobenzene. It will be appreciated that the chosen means of initiation should be substantially incapable of degrading or otherwise adversely reacting with either the reactants or products of the reaction. The amount of catalyst used and the reaction temperature may be varied to suit particular needs, Generally, the polymerization should proceed satisfactorily by carrying out the reaction at a temperature between 25° C. and 100° C. and using less than 5% by weight of initiator, based on the starting weight of the polymerizable monomer or monomers.

The polymers of the present invention, i.e., the polymers of formula (I) can be prepared by resort to an alternative procedure. Thus, if desired, the monomeric polymerizable isocyanatoalkyl ester of formula (IV) can first be polymerized and the resulting polymer can be derivatized by reaction with a substituted alcohol of the formula Z-OH wherein Z has the aforedescribed meaning.

This is illustrated by the following reaction scheme:

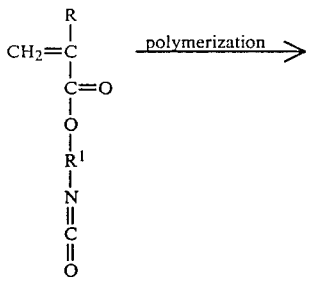

-continued

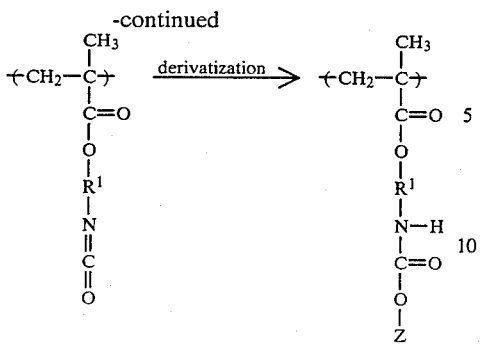

Derivatiaation of the polymeric isocyanatoalkyl esters can be suitably conducted in the presence of an inert and substantially anhydrous solvent such as tetrahydrofuran, benzene, toluene, dioxane, ethyl acetate, methylethylketone, chloroform, or dichloromethane. If desired, the derivatization reaction may be facilitated by the presence of a suitable catalyst as mentioned hereinbefore.

The present invention is further illustrated in the following Examples which are illustrative only and not intended to be of limiting effect. Unless otherwise stated, all parts of percentages are by weight.

EXAMPLE 1

Preparation of N-(methacryloxyethyl)-β-methylsulfonylethyl carbamate (MEMSEC)

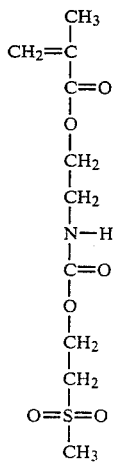

A mixture of 68.2 grams of 2-hydroxyethylmethylsulfone, 50 grams of anhydrous sodium sulfate and 25 grams of 4-Angstrom zeolitic molecular sieve material in 250 mls. of methylene chloride was stirred for 30 minutes in a one-liter, three-necked flask equipped with a stirrer, thermometer and a water condenser topped with a drying tube. To the mixture, 2-isocyanatoethyl methacrylate (70.5 mls.) was added, followed by the addition of 250 mls. of methylene chloride and stirring of the resulting mixture for five minutes. The stirrer was stopped, 6.1 grams of 4-(N,N-dimethylamino) pyridine were added and the resulting mixture was stirred for 12 hours. Addition of the 4-(N,N-dimethylamino) pyridine was observed to cause an exotherm of about 12° C. (25°–37° C.). Progress of the reaction was monitored by using IR analysis for isocyanato absorption (by taking out a drop of reaction solution and putting it between two sodium chloride plates) and by thin layer chromatographic technique. Upon completion of the reaction, the reaction mixture was vacuum filtered (aspirator) and the reaction solids were washed twice with methylene chloride (2×50 mls.). The combined filtrates were stirred with 200 mls. of cold water containing 4 mls. of glacial acetic acid for 30 minutes. The organic phase was separated and washed with water twice (200 mls. of water each time). The organic phase was then washed with 200 mls. of freshly prepared 1% aqueous sodium bicarbonate solution, then with 200 mls. of water, then with 200 mls. of saturated sodium chloride solution and was dried using anhydrous sodium sulfate. Prior to solvent removal, 10 mgs. of 2,6-ditertiary butyl p-cresol were added to the methylene chloride solution and solvent was removed first using a rotary evaporator and then using a vacuum pump. The resulting product was a thick syrupy liquid (129 grams) which on seeding with crystalline monomer and standing turned into a white crystalline solid, m.p. 38°–40° C. The product, soluble in methylene chloride, trichloromethane, acetone, methanol and ethyl acetate was the monomer N-(methacryloxyethyl)-β-methylsulfonylethyl carbamate. Molecular structure was confirmed by resort to proton nuclear magnetic resonance and infrared analytical techniques.

EXAMPLE 2

Preparation of N-(methacryloxyethyl)-β-cyanoethyl carbamate

β-Isocyanatoethyl methacrylate (15.5 grams; 0.1 mole) and β-hydroxypropionitrile (7.1 grams; 0.1 mole) were dissolved in methylene chloride (100 mls.) in a 250 ml., three-necked flask equipped with a stirrer, thermometer and a water condenser topped with a drying tube. To the reaction mixture, 4-(N,N-dimethylamino) pyridine (1.24 grams; 0.01 mole) was added and the contents stirred at ambient temperature for 24 hours. Addition of the 4-(N,N-dimethylamino) pyridine was observed to cause an exotherm of about 12° C. (25°–37° C.). Water (50 mls.) and glacial acetic acid (one ml.) were added and the reaction mixture was stirred for 30 minutes. The organic phase was separated and washed with water twice (50 mls. of water each time). Next, the organic phase was washed with 50 mls. of freshly prepared 1.0% aqueous sodium bicarbonate solution, then, with water (50 mls.), then, with saturated sodium chloride solution (50 mls.) and, then, was dried using anhydrous sodium sulfate. Removal of solvent using a rotary evaporator gave a syrup which on slurrying with n-hexane changed into a crystalline solid (19.4 grams; 85.8%). The product, N-(methacryloxyethyl)-β-cyanoethyl carbamate, exhibited a melting point of 56°–58° C. Molecular structure was confirmed by resort to thin layer chromatographic, proton nuclear magnetic resonance and infrared analytical techniques.

EXAMPLE 3

Preparation of N-(methacryloxyethyl)-β-(p-tolylsulfonyl) ethyl carbamate

β-isocyanatoethyl methacrylate (15.5 grams; 0.1 mole) and p-tolysulfonyl ethanol (20.2 grams; 0.1 mole) were dissolved in methylene chloride (100 mls.) in a 250-ml., three-necked flask equipped with a stirrer, thermometer and a water condenser topped with a drying tube. 4-(N,N-dimethylamino) pyridine (1.24 grams; 0.01 mole) was added and the contents stirred at ambient temperature for 24 hours. The addition of 4-(N,N-dimethylamino) pyridine was observed to cause an exotherm of about 10°–12° C. Water (50 mls.) and glacial acetic acid (one ml.) were added and the mixture stirred for 30 minutes. The organic phase was separated and washed with water twice (using 50 mls. of water each time). Next, the organic phase was washed with 50 mls. of freshly prepared 1% aqueous sodium bicarbonate solution, then, with water (50 mls.), then, with saturated sodium chloride solution (50 mls.) and then dried using anhydrous sodium sulfate. Removal of solvent using a rotary evaporator gave a syrupy residue which on trituration with methanol turned into a crystalline solid. It was filtered, washed with cold methanol and dried in a vacuum oven. Yield of the product, N-(methacryloxyethyl)-$\beta$-(p-tolylsulfonyl)ethyl carbamate was 31.38 grams (88.31%) having a melting point of 86°–88° C. Molecular structure was confirmed by resort to thin layer chromatographic, proton nuclear magnetic resonance and infrared analytical techniques.

EXAMPLE 4

Preparation of N-(methacryloxyethyl)-3-sulfolanyl carbamate

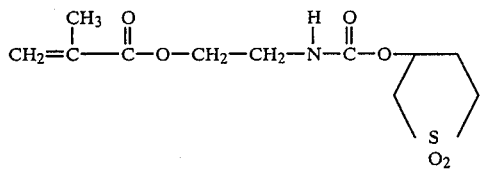

3-hydroxysulfolane (81.70 grams; 0.60 mole) was dissolved in methylene chloride (250 mls.) in a 500-ml., round bottom flash equipped with magnetic stirrer, thermometer and water condenser topped with a drying tube. Anhydrous magnesium sulfate (5.0 grams) and 3-Angstrom, powdered zeolitic molecular sieve material (10.0 grams) were added and the contents were stirred for one hour at room temperature. To the flask was added 8-isocyanatoethyl methacrylate (77.58 grams; 0.50 mole) and 6.11 grams (0.05 mole) of 4-(N,N-dimethylamino)pyridine were added in one portion. The resulting exotherm caused boiling of the methylene chloride and an ice bath was utilized to prevent refluxing. The reaction vessel was cooled for about 1.5 hours and was then stirred at room temperature overnight. Total reaction time was about 22.5 hours. The reaction contents were filtered, then stirred with 200 mls. of ice water and four mls. of glacial acetic acid for one-half hour. The aqueous phase was separated and the organic phase was washed sequentially with water (1×200 mls.), brine (1×200 mls.), 1% sodium bicarbonate solution (1×200 mls.), brine (1×200 mls.) and was dried with magnesium sulfate. The product was decolorize with charcoal, filtered and 15 mgs. of 4-methyl-2,6-ditertbutyl phenol were added. A viscous yellow liquid was recovered after evaporation of solvent in vacuo. The product, which slowly crystallized on standing, was dissolved in a minimum of ethyl acetate (about 600 mls. product provided about 800 mls. of solution). Hexane (600 mls.) was added to the cloud point and the solution was cooled to −20° C. An additional 100°–150 ml. quantity of hexane was added and the solution was again cooled. A white, solid product was recovered by filtration and was washed with hexane, air and, then, vacuum dried to yield 120.74 grams (82.9% yield) of product having a melting point of 70.5°–71.5° C. Molecular structure was confirmed by nuclear magnetic resonance and thin layer chromatographic techniques.

|  | % C | % H | % N | % S | % O |
|---|---|---|---|---|---|
| Calculated for $C_{11}H_{17}NO_6S$ | 45.35 | 5.88 | 4.81 | 11.01 | 32.95 |
| Found | 45.54 | 6.01 | 4.71 | 10.97 | — |

EXAMPLE 5

Preparation of a matrix system comprising a matrix terpolymer consisting of 48.9 parts by weight of diacetone acrylamide, 42.6 parts by weight of butyl acrylate, 8.0 parts by weight of acrylic acid, and 0.5 parts by weight of 2-acrylamido-2-methylpropane sulfonic acid and a $\beta$-elimination copolymer consisting of 80 parts by weight of N-(methacryloxyethyl)-$\beta$-methylsulfonylethyl carbamate and 20 parts by weight of styrene wherein the ratio by weight of matrix polymer to $\beta$-elimination polymer is 78:22.

A mixture of 0.0405 grams of ferrous sulfate heptahydrate, 26.36 grams of a 23.9% by weight dialyzed Dowfax solution (Dowfax 2A1 solution available from the Dow Chemical Company, Midland, Mich.), 16.8 grams of a 100% solution of Triton X-100 (available from Rohm and Haas Corp., Philadelphia, Pa.) and 3.6 liters of water was heated to 65° C. under a nitrogen atmosphere and to this mixture were added simultaneously, in separate streams, over a period of two hours:
(a) a mixture of 1026.8 grams of diacetone acrylamide, 168 grams of acrylic acid, 10.5 grams of 2-acrylamido-2-methylpropane sulfonic acid, 35.15 grams of a 23.9% by weight dialyzed Dowfax solution; and 2.1 liters of water;
(b) 894.7 grams of butylacrylate;
(c) a solution of 7.64 grams of potassium persulfate in 200 milliliters of water; and
(d) a solution of 2.89 grams of sodium bisulfite in 100 milliliters of water.
Following completion of the additions, the mixture was maintained at 65° C. for one hour. The temperature was then lowered to 55° C. and 1311 grams of 1% sodium hydroxide solution and 33 grams of 18% dialyzed Dowfax solution were added over one-half hour.
To the polymeric material prepared as aforedescribed were added simultaneously, in separate streams, over one hour:
(e) a mixture of 492 grams of N-(methacyloxyethyl)-$\beta$-methyl sulfonylethyl carbamate and 118 grams of styrene;
(f) a solution of 4.4 grams of potassium persulfate and 328 milliliters of water; and
(g) a solution of 2.6 grams of sodium bisulfite in 328 milliliters of water.
Following the completion of these additions, the temperature of the mixture was maintained at 55° C. for three hours. Yield of 10.8 kilograms of a matrix system having a solids concentration fo 26% by weight.

EXAMPLE 6

Beta-elimination polymers were evaluated using a test structure, 32 in FIG. 3, comprising a transparent support 33, a layer 34 comprising about 215 mg./m² of a cyan dye developer of the formula

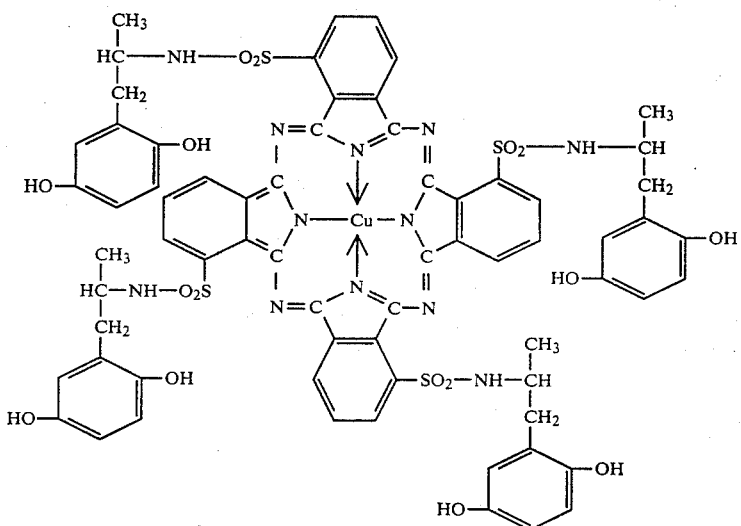

about 430 mg./m.² gelatin, and about 16 mg./m.² of succindialdehyde and a layer 35 containing about 2150 mg./m.² of the polymeric material. Layers 34 and 35 were coated sequentially on support 33 using a conventional loop coater.

A transparent sheet 37 comprising a polyester clear film base was superposed with test structure 32 and an opaque alkaline processing composition 36 comprising:

| | |
|---|---|
| Potassium hydroxide (45% aqueous solution) | 23.94 g. |
| Benzotriazole | 1.33 g. |
| 6-Methyl uracil | 0.73 g. |
| Bis-(β-aminoethyl)-sulfide | 0.06 g. |
| Colloidal silica, aqueous dispersion (30% SiO₂) | 4.48 g. |
| Titanium dioxide | 92.12 g. |
| N—phenethyl α-picolinium bromide (50% aqueous solution) | 6.18 g. |
| N—2-hydroxyethyl-N,N'N'—triscarboxymethyl ethylene diamine | 1.82 g. |
| 4-Amino pyrazolo(3,4d)pyrimidine | 0.61 g. |
| Carboxymethyl hydroxyethyl cellulose | 4.82 g. |
| Water | 100 g. | was introduced between polymeric test material layer 35 and transparent sheet 37 at a gap of 0.071 mm. Immediately after introduction of the processing composition the optical reflection density to red light of the sample was monitored through transparent support 33 as a function of time by use of a MacBeth Quanta-Log densitometer equipped with a strip-chart recorder. The density measured as a function of time was that of the cyan dye developer in the original dye-containing layer 34 and the cyan dye developer in polymer test layer 35. Dye developer which had diffused through test layer 35 into the processing composition was masked by the titanium dioxide contained therein and, thus, did not contribute to the red absorption. In this manner, the diffusion of dye developer through the test layer and into the processing composition could be monitored.

Figure 4:
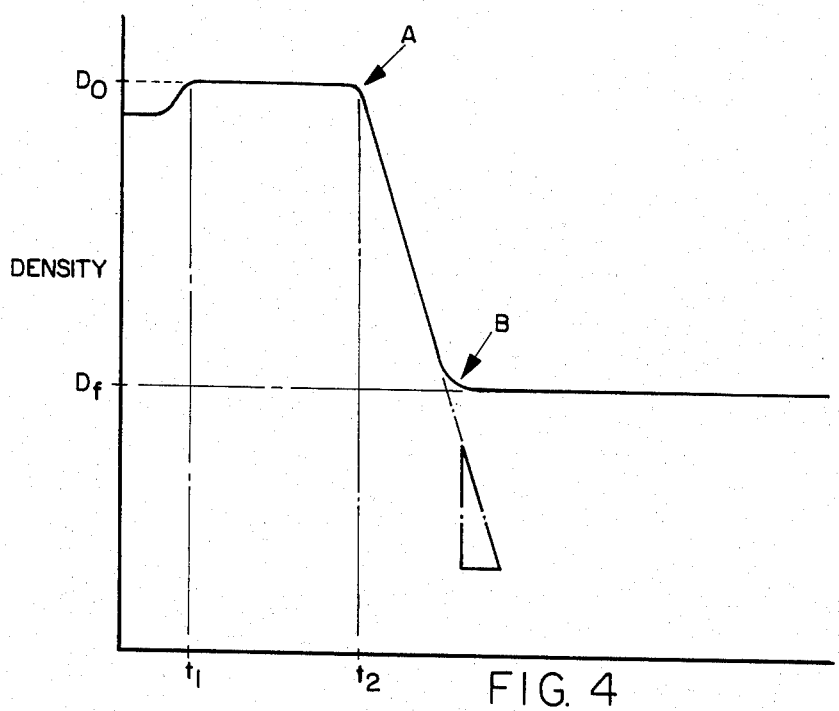
FIG. 4 is a graphical depiction of dye density as a function of time in a system including an interlayer of the present invention.

In FIG. 4 is shown a curve of red absorption density as a function of time where $t_1$ is the time for the cyan dye developer to become wetted by the processing composition, $t_2$ is the total time the cyan dye developer is held back by the polymer interlayer, $D_o$ is the absorption density after dissolution of the dye developer, and $D_f$ is the final absorption density of the residual dye developer remaining in layers 34 and 35 after completion of dye diffusion. The slope of the line segment between A and B is calculated and serves as an indication of the rapidity with which the test layer undergoes a change in dye permeability.

The polymeric material prepared as described in EXAMPLE 5 herein was coated and evaluated as test layer 35 in the above-described test structure. In Table I, the values for $t_1$ and $t_2$ (in seconds) and slope are reported. The polymeric material of EXAMPLE 5 is referred to in Table I as Component X. Mixtures of Component X and Component Y (a copolymer of diacetone acrylamide/butylacrylate/acrylic acid/2-acrylamido-2-methylpropane sulfonic acid (50.5/44/5/0.5 parts by weight, respectively) were also evaluated in the same manner. The mixtures of Components X and Y were tested at weight proportions of 80/20, 65/35 and 55/45. Results are reported in Table I.

TABLE 1

| Polymeric Product | $t_1$ | $t_2$ | Slope |
|---|---|---|---|
| Product of EXAMPLE 5 (Component X) | 0.5 | 16 | 377 |
| 80/20 Mixture of Components X and Y | <0.5 | 18 | 356 |
| 65/35 Mixture of Components X and Y | <0.5 | 21 | 288 |
| 55/45 Mixture of Components X and Y | <0.5 | 27 | 92 |

EXAMPLE 7

The above-described test structure and procedure were utilized to evaluate matrix polymer/β-elimination polymer systems referred to hereinbefore as Matrix Systems A, B and C. Results of the evaluations are reported in Table 2 as follows:

TABLE 2

| Matrix System | $t_1$ | $t_2$ | Slope |
|---|---|---|---|
| A | 0 | 33 | 204 |
| B | 0 | 16 | 390 |
| C | 1 | 16 | 425 |
| E | 0.5 | 61 | 135 |

EXAMPLE 8

Preparation of a matrix system comprising a matrix terpolymer consisting of 48.9 parts by weight of diacetone acrylamide, 42.6 parts by weight of butyl acrylate, 8.0 parts by weight of acrylic acid, and 0.5 parts by weight of 2-acrylamido-2-methylpropane sulfonic acid and a β-elimination copolymer consisting of 80 parts by weight of N-(methacryloxyethyl)-3-sulfolanyl carbamate and 20 parts by weight of methyl methacrylate wherein the ratio by weight of matrix polymer to β-elimination polymer is 70:30.

A polymeric matrix was prepared according to the procedure set forth in EXAMPLE 5 except as follows. Upon completion of the addition of streams (a) through (d), 274.5 grams of the resulting matrix polymer were treated in the following manner. Five grams of water and 1.08 grams of 18% dialyzed Dowfax solution were added to the polymer matrix. The matrix was purged with nitrogen and the temperature was raised to 55° C. Over a period of about 20 minutes, 51.5 grams of 1% sodium hydroxide solution were added in a dropwise manner. The resulting neutralized matrix polymer was held under a nitrogen atmosphere for 30 minutes.

To the neutralized polymeric matrix material prepared as aforedescribed were added simultaneously, in separate streams, over about 45 minutes:

(e) a mixture of 24.18 grams of N-(methacryloxyethyl)-3-sulfolanyl carbamate and 5.82 grams methyl methacrylate;

(f) a solution of 0.2183 gram of potassium persulfate and 20 milliliters of water; and (g) a solution of 0.1293 gram of sodium bisulfite in 20 milliliters of water.

Following completion of these additions, the temperature of the mixture was maintained at 55° C. for three hours. Yield of 402 grams of a matrix system having a solids concentration of 25.3% by weight.

The product resulting from the procedure of EXAMPLE 8 was evaluated using the test structure and procedure set forth in EXAMPLE 6. The results are reported in Table 2 hereinbefore and identified therein as Matrix System E.

EXAMPLE 9

A photographic film unit according to the present invention was prepared in the following manner. A transparent polyethylene terephthalate support was coated in succession with the following layers:

1. as a polymeric acid layer, approximately 8.5 parts of a half butyl ester of polyethylene/maleic anhydride copolymer and one part of polyvinyl butyral, coated at a coverage of about 26,372 mgs./m.$^2$;

2. as a timing layer, coated at a coverage of about 1750 mgs./m$^2$, a 39/39/1.5/0.5/20 (parts by weight) copolymer of diacetone acrylamide/ butyl acrylamide/acrylic acid/2-acrylamido-2-methylpropane sulfonic acid/2-cyanoethyl acrylate;

3. a blue-sensitive silver iodobromide emulsion layer comprising about 1000 mgs./m.$^2$ of silver (1.1 microns) and about 500 mgs./m.$^2$ of gelatin;

4. a yellow dye developer layer comprising about 1150 mgs./m.$^2$ of a yellow dye developer represented by the formula

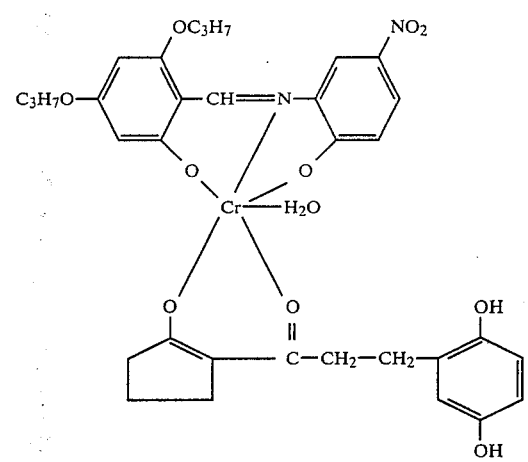

about 541 mgs./m.$^2$ of gelatin and about 115 mgs./m.$^2$ of 4'-methylphenyl hydroquinone;

5. an interlayer comprising a mixture of 55 parts of 50.5/44/5/0.5 copolymer of diacetone acrylate/butyl acrylate/acrylic acid/2-acrylamido-2-methylpropane sulfonic acid and 45 parts of a matrix system consisting of 78 parts of 48.9/42.6/8/0.5 matrix copolymer of diacetone acrylamide/butyl acrylate/acrylic acid/2-acrylamido-2-methylpropane sulfonic acid and 22 parts of 80/20 poly(N-methacryloxyethyl-β-methylsulfonylethylco-styrene), the mixture at a coverage of about 2000 mgs./m.$^2$; and about 48.3 mgs./m$^2$ of succindialdehyde;

6. a green-sensitive silver iodobromide emulsion layer comprising about 896 mgs./m.$^2$. of silver (1.1 microns) and about 394 mgs./m.$^2$ of gelatin;

7. a magenta dye developer layer comprising about 500 mgs./m.$^2$ of a magenta dye developer represented by the

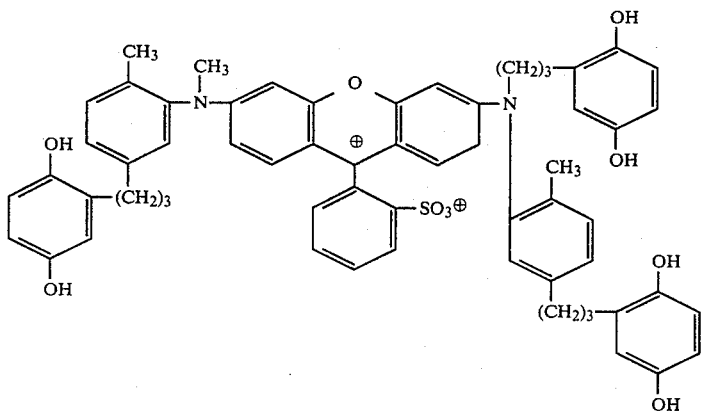

about 318 mgs./m.² of gelatin and about 177 mgs./m.² of 4'-methylphenyl hydroquinone;

8. an interlayer comprising the mixture of layer 5 hereinbefore, at a coverage of about 1500 mgs./m.²; and about 36.2 mgs./m.² of succindaildehyde;

9. a red-sensitive silver iodobromide emulsion layer comprising about 866 mgs./m.² of silver (1.1 microns) and about 520 mgs./m.² of gelatin;

10. a cyan dye developer layer comprising about 350 mgs./m.² of a cyan dye developer represented by the formula

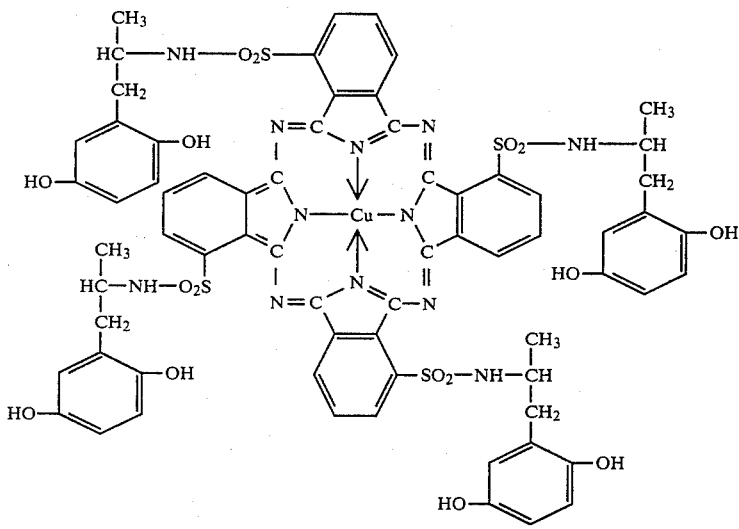

about 263 mgs./m.² of gelatin and about 100 mgs./m.² of 4'-methylphenyl hydroquinone;

11. an interlayer comprising the mixture of layer 5 hereinbefore, at a coverage of about 1750 mgs./m.²;

12. a light-reflecting pigment layer comprising about 9000 mgs./m.² of titanium dioxide; about 1352 mgs./m.² poly(ethylene oxide); and about 600 mgs./m² of particulate poly(tetrafluoroethylene); and 13. an image-receiving layer comprising about 2000 mgs./m.² of a graft copolymer of 4-vinylpyridine(4VP) and vinylbenzyl trimethyl ammonium chloride(TMQ) grafted onto hydroxyethyl cellulose(HEC) at a ratio of HEC/4VP/TMQ of 2.2/2.2/1.

The above-described film unit was tested photographically at room temperature in the following manner. The film unit was photoexposed through the support thereof using a 2 meter-candle-seconds exposure through a test wedge. The photoexposed film unit was brought into superposed relation to a clear polyester spreader sheet with a rupturable container (retaining photographic processing composition) being positioned therebetween. The resulting sandwich was passed through rollers gapped at 0.061 mm. so as to uniformly spread the processing composition with the aid of the spreader sheet. After a five-minute inbibition period (in the dark at room temperature), the resulting photograph with stripper sheet left intact was removed to ambient light for viewing the photographic image through the spreader sheet.

The photographic processing composition utilized for the evaluation contained the following ingredients at the stated weight percentages as follows:

| | |
|---|---|
| Water | 88.6 |
| Potassium hydroxide | 5.9 |
| Benzotriazole | 0.24 |
| 6-Bromo-5-methyl-4-azabenzimidazole | 0.10 |
| Phenylmercapto tetrazole | 0.047 |
| 6-Methyl uracil | 0.096 |
| 4-Amino-pyrazolo(3,4d)pyrimidine | 0.23 |
| N—Phenethyl-2-picolinium bromide | 1.57 |
| Hydroxyethyl cellulose | 3.1 |

| -continued | |
|---|---|
| 4,4'-Isopropylidene diphenol | 0.09 |

Maximum and minimum reflection densities were measured and are reported as follows in Table 3.

TABLE 3

|  | Red | Green | Blue |
|---|---|---|---|
| $D_{max}$ | 1.73 | 2.08 | 1.94 |
| $D_{min}$ | 0.25 | 0.20 | 0.23 |

What is claimed is:

1. A polymer comprising recurring units having the formula

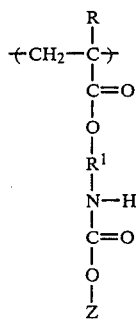

wherein R is hydrogen, halogen or lower alkyl; $R^1$ is alkylene; and Z is an organic moiety capable under alkaline conditions of undergoing a β-elimination reaction, said moiety containing at least two interbonded carbon atoms, one of the carbon atoms containing an acid-labile proton capable of abstraction under said alkaline conditions and an activating group effective to activate said β-elimination reaction.

2. The polymer of claim 1 wherein said moiety Z is a β-elimination moiety of the formula

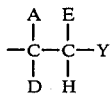

wherein A, D and E are independently hydrogen, methyl or phenyl, provided that not more than one of A, D and E is methyl or phenyl and Y is an activating group for said β-elimination.

3. The polymer of claim 2 wherein said β-elimination activating group Y is selected from the group consisting of sulfones of the formula —SO$_2$W wherein W is aryl, aralkyl, alkaryl, alkyl, amino, or substituted amino; carbonyl groups of the formula

wherein T is hydrogen, alkyl, alkoxy, amino, or substituted amino; sulfoxide groups of the formula

wherein G is aryl, alkyl, alkaryl, or aralkyl; nitro and cyano.

4. The polymer of claim 2 wherein each of A, D and E is hydrogen.

5. The polymer of claim 4 wherein $R^1$ is ethylene.

6. The polymer of claim 2 wherein Y is —SO$_2$W wherein W is alkyl.

7. The polymer of claim 2 wherein R is methyl, $R^1$ is ethylene, each of A, D and E is hydrogen and Y is methylsulfonyl.

8. The polymer of claim 1 wherein said moiety Z is a β-elimination moiety of the formula

wherein Y is a divalent radical

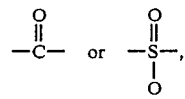

A represents the atoms necessary with Y to complete a four- to seven-membered ring structure, and D and E are independently hydrogen, methyl or phenyl, provided that not more than one of D and E is methyl or phenyl.

9. The polymer of claim 8 wherein D and E are each hydrogen, Y is

 and

A is —CH$_2$—CH$_2$—.

10. The polymer of claim 9 wherein R is methyl and $R^1$ is ethylene.

* * * * *